United States Patent [19]

Dulebohn et al.

[11] Patent Number: 4,823,792

[45] Date of Patent: Apr. 25, 1989

[54] GRIPPING DEVICE AND LOCKING MECHANISM FOR USE THEREWITH

[75] Inventors: David H. Dulebohn, Tonka Bay; David J. Ackland, Maple Grove, both of Minn.

[73] Assignee: Andrew Tool Company, Plymouth, Minn.

[21] Appl. No.: 49,207

[22] Filed: May 11, 1987

[51] Int. Cl.⁴ .............................................. A61B 17/28
[52] U.S. Cl. .................................... 128/321; 128/318; 128/322; 128/340; 128/354; 81/322; 81/416; 294/99.2
[58] Field of Search ............... 128/321, 322, 323, 340, 128/318, 354; 81/415, 416, 417, 322, 323; 294/99.2

[56] References Cited

U.S. PATENT DOCUMENTS

| 397,389 | 2/1889 | Richards | 81/416 X |
|---|---|---|---|
| 2,619,965 | 12/1952 | Goldstone . | |
| 2,632,661 | 3/1953 | Cristofv | 128/321 |
| 2,652,832 | 9/1953 | Castroveijo . | |
| 3,550,595 | 12/1970 | Laufe . | |
| 4,099,315 | 7/1978 | Pudenz | 81/416 X |
| 4,452,246 | 6/1984 | Bader et al. . | |
| 4,478,221 | 10/1984 | Heiss . | |

FOREIGN PATENT DOCUMENTS

| 1119783 | 12/1961 | Fed. Rep. of Germany | 81/416 |
|---|---|---|---|
| 2119695 | 11/1983 | United Kingdom | 81/417 |

OTHER PUBLICATIONS

Mueller Surgical Instrument Catalog (1980), pp. 492, 493.

Primary Examiner—Michael H. Thaler
Attorney, Agent, or Firm—Zarley McKee, Thomte, Voorhees & Sease

[57] ABSTRACT

A clamping device which includes a pair of elongated members which are pivotably but releasably connected. A pivot mechanism exists between gripping ends and handle ends of the elongated members. Female and male members comprise a box hinge whereby the cam holds the elongated members in a secure but pivotable relationship between a closed position for the gripping ends and a maximum open position. If the elongated members are moved beyond the maximum open position, the male cam member can be separated from the female receptor member.

17 Claims, 2 Drawing Sheets

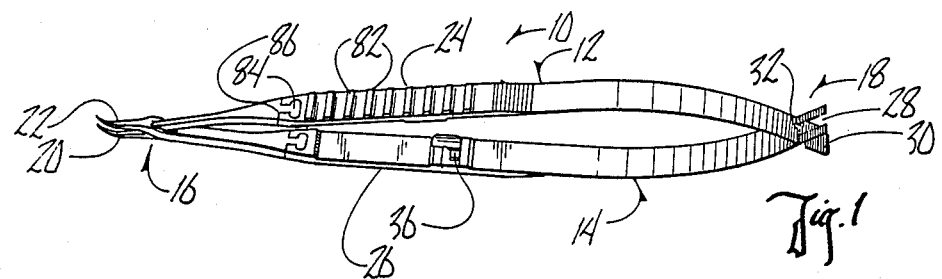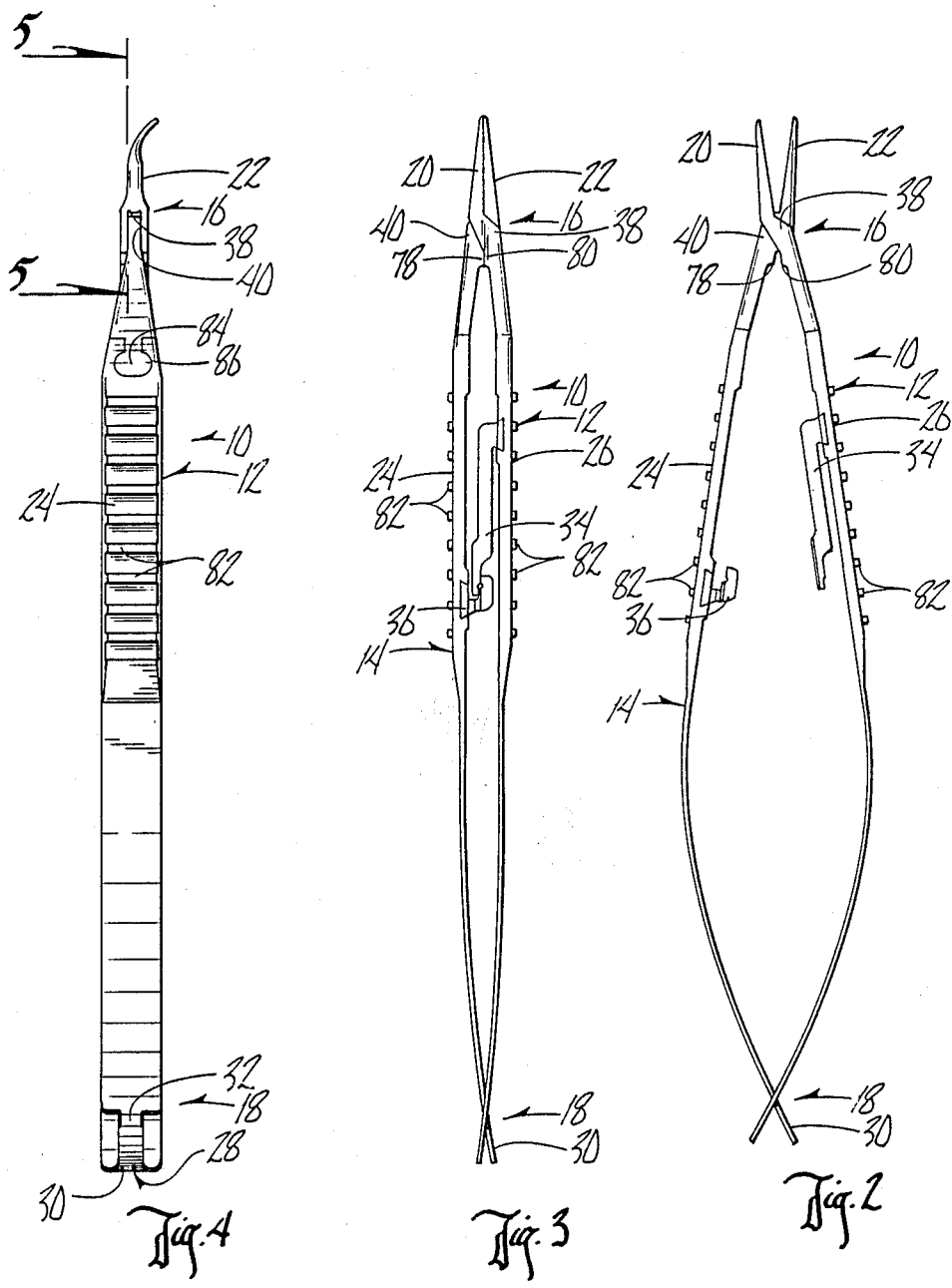
Fig. 1
Fig. 4
Fig. 3
Fig. 2

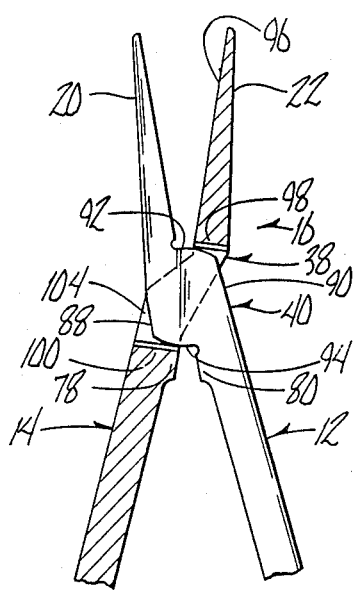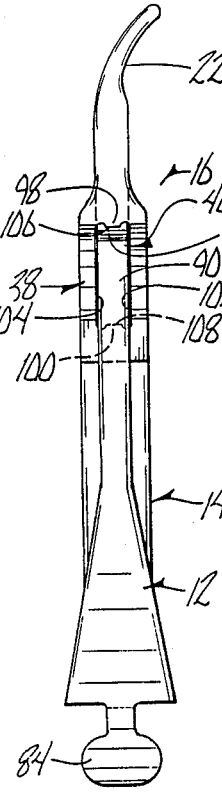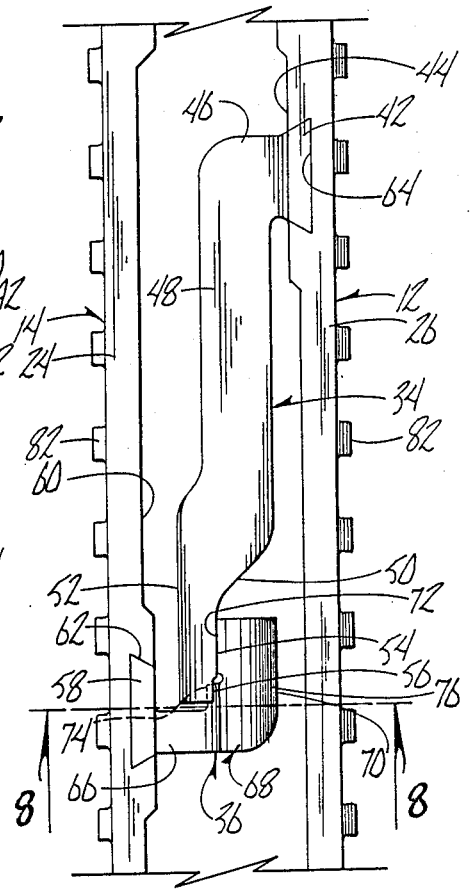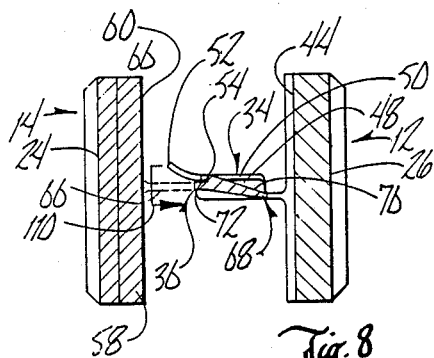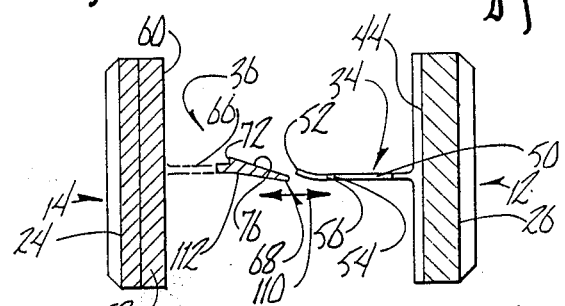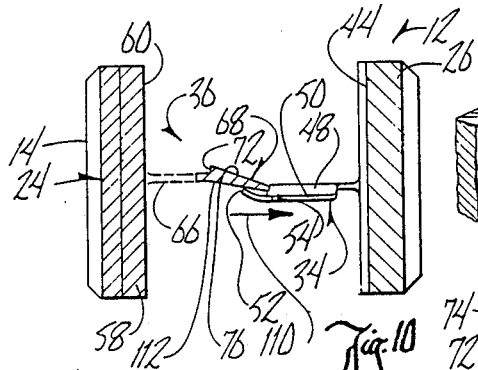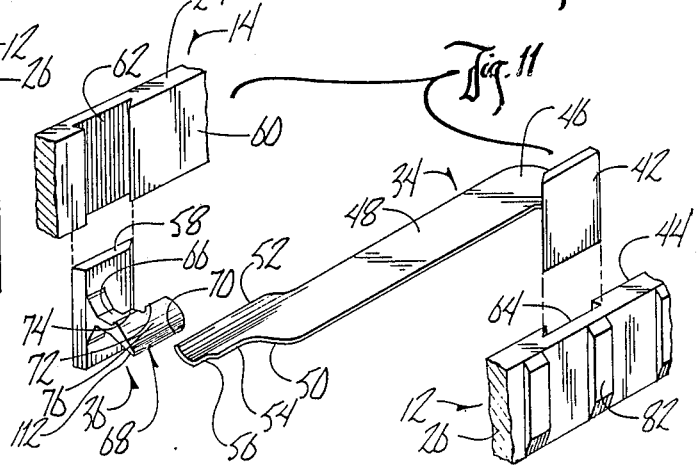

GRIPPING DEVICE AND LOCKING MECHANISM FOR USE THEREWITH

BACKGROUND OF THE INVENTION a. Field of the Invention

This invention relates to a clamping means, and in particular, an easily disassemblable and assemblable clamping means.

b. Problems in the Art

There presently exist many types of clamping devices for many different types of tasks. Some clamping devices, such as tweezers, needle holders, and the like used in medical surgery, require high precision along with durability. Additionally, such instruments must be sterilized and cleaned on a regular basis.

Most conventional clamping devices of these types utilize either permanent securing hardware such as a rivet or the like to join the two pivoting halves and to serve as a pivot point. Other conventional mechanisms utilize a screw or other independent structure for this purpose.

A significant problem exists in that debris and material tend to accumulate between the pivoting halves at the pivoting joint after a period of use. Such accumulation not only can affect the performance of the mechanism, but can actually hinder or inhibit full operability. Material can build up between the pivoting halves and even into any apertures or joints, such as where a rivet or screw is inserted. This can impede or prohibit the disassembling of these devices.

For full operability and cleanliness, such foreign material must be removed. If the pivoting halves are permanently secured together, it is almost impossible to remove such debris. Also, even if a screw or other removable part is used to secure the blades, the debris can be so corrosive and debilitating that it may make it difficult to remove the part to allow separation of the halves for cleaning.

Therefore, a real and significant need exists for a clamping device of the type described which not only is a reliable and durable instrument, but is also easily disassemblable and assemblable for cleaning, repair, and the like. Such a mechanism is needed which has high repeatability, accuracy, strength, and rigidity, while not requiring tools or other significant dismantling operations for separating and cleaning the device.

It is therefore a primary object of the present invention to improve upon or solve the problems in the art.

A further object of the present invention is to provide a clamping device which is easily disassemblable and assemblable.

Another object of the invention is to provide a clamping mechanism which is easily disassemblable and assemblable and yet has a strong, reliable pivot.

A further object of the present invention is to provide a clamping mechanism which is easily and quickly cleanable or repairable.

A further object of the present invention is to provide a clamping device which is easily disassemblable and assemblable, yet is capable of precise, reliable and stable clamping performance.

Another object of the present invention is to provide a clamping means which can be easily and selectively locked in a clamping position.

These and other objects, features, and advantages of the present invention will become apparent with reference to the accompanying specification and drawings.

SUMMARY OF THE INVENTION

The present invention utilizes a pair of elongated members which are pivotally but releasably connected. On one side of a pivot mechanism are the gripping ends of the elongated members; and on the other side of the pivot are the handle ends. An object is gripped by converging the handle members which in turn converges the gripping ends.

The pivot mechanism for the device includes a female receptor integrally formed along the length of one elongated member, and a male cam member integrally formed along the length of the other elongated member. The other elongated member is passed through the female receptor until the cam member is positioned therein. The gripping ends of the clamping device are operable through a range from a closed position, where the gripping ends are in abutment or closely adjacent to one another, and then over a range of open positions to a maximum open position.

The female receptor and cam member are configured so that if the pair of elongated members are angularly disposed at an angle greater than the maximum open position, the cam member can be removed from or inserted into the female receptor. Upon general positioning and converging of the handles to the maximum open position, the female receptor then retains the cam member therein, forming a strong and reliable pivot over the range of open positions down to a closed position. The elongated members are easily disassembled by diverging the handles past the maximum open position whereby the cam is easily removed from the female receptor, and the elongated members are easily separated.

In a preferred embodiment, the pivot mechanism is a box hinge wherein the female receptor is a rectangular box-shaped aperture, and the male member is a circle having generally opposite truncated sides and generally opposite arcuate bearing surfaces. The male member fits within the rectangular box, the ends of the box along its long axis serving as conforming bearing surfaces to the arcuate portions of the male cam member.

In an alternative embodiment, the rearward portions of the handles can include a releasable connection which serves to bow the rearward ends of the handles and separate the handles, which in turn biases the gripping ends to a normally open position. A still further embodiment utilizes a locking mechanism between the handles which allows the gripping members to be locked in a closely adjacent or abutting gripping position.

The locking mechanism consists of one arm which extends perpendicularly outward for distance from an interior facing surface of one handle and then rearwardly generally along the longitudinal axis of the handle. It is deflectable transversely to the longitudinal axis of the handle and contains an end portion which has a catching edge. A complementary member extends inwardly from the inside facing surface of the other handle, having a first portion extending perpendicularly outward, and then a second portion extending forwardly along the longitudinal axis of the second handle member in an opposite direction to that of the first locking mechanism part. The second locking mechanism part presents a thin outward edge which travels slightly to one side of the outer end of the first locking mechanism part when the instrument handles are converged. It then has a sloping surface which presents increasingly thickened or angled surface which culminates in a catcher edge. Thus, when the handles are converged together, the second locking mechanism part, with its leading edge, passes by the outer end of the first locking mechanism part. The first locking mechanism part then abuts and slides along the sloping surface, which deflects the first part away from its normal position. If the handles are slowly converged as the catching edge moves up upon the catcher edge, and convergence is stopped when the catching edge moves up on top of the catcher edge, the handles will be locked in position, as will the gripping ends of the clamping device. Slight further convergence of the handles will then release the first locking mechanism part as it will travel back to its original position past around the catcher edge. Therefore, if clamping is desired without locking, the handles are converged so that the first locking mechanism part rotates past the second locking mechanism part.

In other embodiments, it is to be understood that each elongated member can be comprised of two sections, a forward section and a rearward section. The forward sections are separable from the rearward sections so that the gripping ends, the pivot section, and part of the handle ends can be removed and replaced. The front sections are secured to the rear sections of the elongated members by interference fitting a key member on one section into a slot on the other.

BRIEF DESCRIPTION OF THE DRAWINGS

FIG. 1 is a perspective view of a preferred embodiment of the invention.

FIG. 2 is a side view of the embodiment of FIG. 1, shown in a normally biased open position.

FIG. 3 is a side view of the embodiment of FIG. 1, showing the clamping mechanism in a locked closed position.

FIG. 4 is a top view of the embodiment of FIG. 1.

FIG. 5 is an enlarged partial sectional view taken along lines 5—5 of FIG. 4.

FIG. 6 is an enlarged isolated view of the first forward section of the embodiment of FIG. 4.

FIG. 7 is an isolated and enlarged side view of the locking mechanism of the device.

FIG. 8 is a sectional view taken along lines 8—8 of FIG. 7.

FIG. 9 is a sectional view similar to FIG. 8 but showing the opposite arms of the locking mechanism disengaged engaged and spaced apart.

FIG. 10 is a sectional view similar to FIG. 8 showing the opposite arms of the locking mechanism just after release from locking engagement.

FIG. 11 is an enlarged isolated perspective view of the opposite locking arms of the locking mechanism.

DETAILED DESCRIPTION OF THE PREFERRED EMBODIMENT

With reference to the drawings, and particularly FIG. 1, there is shown a clamping device 10 in accordance with the invention. For purposes of illustration, clamping device 10 is a needle holder of the type used in medical surgery. It consists of a pair of elongated members 12 and 14 which are pivotally connected at a pivot means generally indicated by reference numeral 16. In this embodiment, device 10 also includes a releasable connection, generally indicated by reference numeral 18 at its rearward end.

Each elongated member 12 and 14 includes a gripping end 20 and 22, and a handle end 24 and 26, respectively. Pivot means 16 allows converging movement of handle ends 24 and 26 to cause converging movement of gripping ends 20 and 22, to perform the clamping function of device 10.

Releasable connection 18 consists of a slot 28 extending inwardly from the rearward end of elongated member 14, and a T-shaped head on the rearward end of elongated member 12. The narrow leg 32 of T-shaped head 30 fits within slot 28 to create a frictional and binding connection between the rear ends of elongated members 12 and 14, which are curved or slightly bent to achieve the releasable connection 18. The bend or curve in the rearward parts of elongated members 12 and 14 causes handle ends 24 and 26 to be separated to a point that gripping ends 20 and 22 are biased to a normally open position. If inward converging forces on handles 24 and 26 are released, gripping ends 20 and 22 would therefore revert to the normally open position.

FIG. 1 also partially depicts a locking mechanism consisting of a first locking part 34 (see FIG. 2), and a second locking part 36. This locking mechanism allows the gripping ends 20 and 22 to be locked in a clamping or gripping position by selection of the user of clamping device 10, and then released upon desire. The locking mechanism also allows the user to by-pass it if no locking function is desired when handles 12 and 14 are converged together.

The pivot means 16 for clamping device 10 not only performs repeatable, accurate, reliable and strong pivoting of elongated members 12 and 14, but also allows easy and quick disassembling and assembling of members 12 and 14. This is accomplished in that pivot means 16 is basically a box hinge whereby elongated member 14 includes a female receptor means 38 formed integrally along its length, and elongated member 12 includes a male cam means 40 integrally formed along its length. Elongated member 12 is insertable through female receptor means 38 until male cam means 40 is generally positioned therein. By appropriate orientation of elongated member 12 to elongated member 14, male cam means 40 can then be retained within female receptor means 38 during the normal pivoting range of motion of device 10 to provide pivoting action for device 10.

It is to be understood that the normal pivoting movement of elongated members 12 and 14 is between a closed position where gripping ends 20 and 22 are in abutment or closely adjacent, and then through a range of open positions to a maximum open position. Female receptor means 38 and male cam means 40 are constructed so that when elongated member 12 is angularly oriented towards elongated member 14 past the maximum open position, male cam means 40 is released from retainment in female receptor means 38 and members 12 and 14 can be quickly and easily separated by pulling elongated member 12 from out of female receptor means 38 and elongated member 14. Assembly of members 12 and 14 is easily accomplished by the reverse process.

FIGS. 2-4 show the general configuration of clamping device 10. In particular, FIG. 2 shows device 10 in its normally open position with gripping ends 20 and 22 biased apart. FIG. 2 also shows in better detail the first locking part 34 and second locking part 36 of the locking mechanism for device 10.

It is also pointed out that in the preferred embodiment shown in FIGS. 2 and 3, each elongated member 12 and 14 includes fulcrum members 78 and 80, respectively, which consists of raised portions. As can be seen in FIG. 3, when the clamping device 10 is moved towards a closed position, fulcrum members 78 and 80 come into abutment and serve as the fulcrum for the device. When an object is gripped by gripping ends 20 and 22, fulcrum members 78 and 80 experience the majority of pivotal force and prevent gapping or springing of gripping ends 20 and 22. Fulcrum members 78 and 80 also prevent over-rotation of elongated members 12 and 14 with respect to one another.

FIG. 4 depicts additional views of features of clamping device 10 including projections 82 along the handles (see also FIGS. 1-3) which facilitates gripping of clamping device 10. FIG. 4 also shows that optionally the front section of clamping device 10, that being the front sections of elongated members 12 and 14, can be removable from the rearward portions which basically comprise most of the handle. A key member 84 is formed integrally along each elongated member 12 and 14 and is fittable into the corresponding slot 86 in each member 12 and 14. It is preferred that key members 84 are interference fit into slots 86; that being that the circumference of key members 84 is slightly larger than the diameter of slot 86 but that the natural resiliency of the material allows keys 84 to be forcibly fit into slots 86 and held securely therein. This feature allows the forward ends of such devices to be interchanged, replaced, repaired, and also allows for manufacturing savings. Different ends can be used with different handles, and if an end is damaged, only it needs to be replaced, not the entire handle.

FIGS. 5 and 6 present more detailed views of the preferred embodiment of pivot means 16. In FIG. 5, it can be seen that male cam means 40 is generally a circle having generally opposite truncated sides 88 and 90. Its remaining edge surfaces are arcuate bearing surfaces 92 and 94 and comprise basically the front and rear of cam means 40. It can be seen that cam means 40 is therefore longer from arcuate bearing surface 92 to surface 94 than from truncated side 88 to side 90. Thus, in FIG. 5, when elongated member 12 is angularly disposed to elongated member 14 such that truncated surface 90 passes to the left of edge 96 of elongated member 14, and truncated side 88 passes to the right of fulcrum member 80 of elongated member 14, cam means 40 can be removed from female receptor means 38.

When cam member 40 is retained within female receptor means 38, arcuate bearing surfaces 92 and 94 define the range of positions between the closed position and a maximum open position. Pivoting elongated member 12 to the position where it can be removed from female receptor means 38 is equivalent to moving it past the maximum open position.

FIG. 5 shows front wall 98 and rear wall 100 of female receptor means 38. It can be seen that front and rear walls 98 and 100 present corresponding bearing surfaces to arcuate bearing surfaces 92 and 94 of male cam means 40. When device 10 is between a closed position and a maximum open position, elongated member 12 is retained within female receptor means 38. As FIG. 6 shows, female receptor means 38 is basically a rectangular box aperture having front wall 98, rear wall 100 and side walls 102 and 104. Additionally, in the preferred embodiment, front and rear walls 98 and 100 have raised middle portions 106 and 108 which provide the actual bearing surfaces against arcuate bearing surfaces 92 and 94 of cam means 40.

The box aperture is configured so that the width of cam means 40 is within a close tolerance of side walls 102 and 104 to prevent any lateral movement between elongated members 12 and 14. FIG. 5 also shows that when cam member 40 is within female receptor means 38, the arcuate bearing surfaces 92 and 94 limit any side-to-side movement between elongated members 12 and 14 from that position. Indeed, cam means 40 is "boxed in", because movement past a closed position is stopped by the abutment of gripping ends 20 and 22, and fulcrum members 78 and 80. Release of cam means 40 from female receptor means 38 is only accomplished when elongated member 12 is rotated past the maximum open position defined by arcuate bearing surfaces 92 and 94. FIG. 6 also shows the preferred embodiment of key member 84 for the upper portion of device 10.

FIG. 7 shows an enlarged view of the locking mechanism as shown in FIG. 3. The first locking part 34 includes a base 42 which is secured into the innerfacing surface 44 of handle 26. A first portion 46 extends generally perpendicularly outward from surface 44. A second portion 48 extends generally rearwardly spaced apart from surface 44, but generally along the longitudinal axis of handle 26. Second portion 48 is deflectable laterally to the longitudinal axis of handle 26. It can be made of thin stainless steel or other suitable material. An outer end 50 includes a leading edge 52 which is somewhat raised from second portion 48, and a catching edge 54 opposite from leading edge 52. Edges 52 and 54 are generally parallel to inner facing surface 44. A notch 56 is also included in the preferred embodiment of catching edge 54 at its outermost tip.

The second locking part 36 also contains a base 58 which is secured in inner-facing surface 60 of handle 24. Both base 42 and base 58 are secured within generally matable slots 62 and 64 in their respective handles 24 and 26. In the preferred embodiment, bases 42 and 58 are interference fit into slots 62 and 64.

A first portion 66 extends from base 58 generally perpendicularly from inner-facing surface 60. A head portion 68 then extends generally parallel and spaced apart to the longitudinal axis of handle 24, but forwardly towards pivot means 16. This is in the opposite direction that second portion 48 of first locking port 34 extends. Head portion 68 includes a leading edge 70 and a catcher edge 72 opposite therefrom. Catcher edge 72 includes a raised portion 74, which in this embodiment extends from first portion 66 along catcher edge 72.

FIG. 3 shows the first and second locking parts 34 and 36 in a locked position. Locking is accomplished by first moving handles 24 and 26 convergingly towards each other. Leading edge 70 of second locking part 36 is positioned to be slightly to the side of leading edge 52 of first locking part 34 so that when two leading edges 52 and 70 come into closely adjacent positions, upon further convergence of handles 24 and 26, leading edge 70 would pass leading edge 52. Leading edge 52 would then contact sloped surface 76 on head portion 68 of second locking portion 36. Sloped surface 76 deflects outer end 50 of first locking part 34 from its normal position. Upon further convergence of handles 24 and 26, leading edge 52 passes by catcher edge 72 of second locking part 36; but then catching edge 54 of first locking part 34 would approach catcher edge 72. By slowing down convergence of handles 24 and 26, catching edge 54, upon just passing over catcher edge 72 would begin deflection back to its normal position. However, raised portion 74 along catcher edge 72 would stop complete deflection back to normal position of first locking part 3, and if convergence of handles 24 and 26 is then stopped, would hold or lock locking parts 34 and 36 (and thus handles 24 and 26 and gripping ends 20 and 22) in basically a closed position.

To release the locking mechanism, the user only has to slightly further converge handles 24 and 26 so that catching edge 54 travels over and bypasses raised portion 74 of catcher edge 72. By the natural returning properties of first locking part 34, which is no longer deflected, first locking part 34 would then be able to pass clear of second locking part 36 when converging pressure on handles 24 and 26 is released. It is again to be understood that releasable connection 18 biases handles 24 and 26 to the position shown in FIG. 22.

Therefore, it is to be understood that outer end 50 of first locking part 34 basically circles around head portion 68 of second locking part 36. If the user does not wish to lock the clamping device 10, converging pressure is sufficiently applied to handles 24 and 26 that first locking part 34 is deflected and then bypasses second locking part 36.

FIG. 8 shows in further detail the sloped surface 76 of head portion 68 of second locking part 36. It also shows that head portion 68 is angled from first portion 66 in an opposite direction to the slight angle on leading edge 52 of first locking part 34. This is also shown at FIG. 9.

FIG. 8 shows how first locking port 34 would then continue and catching edge 54 would lock upon catcher edge 72. Arrow 110 in FIG. 8 depicts how first locking part 34 would continue past and return around the other side of second locking part 36 upon continued convergence of handles 24, 26 and then divergence of handles 24 and 26.

FIG. 9 depicts the normal position of second portion 48 of first locking part 34 and that when handles 26 and 24 converge, leading edge 52 passes by leading edge 70 and comes upon sloped surface 76.

FIG. 10 shows upon divergence, first locking part 34 would actually slide past surface 112 which is opposite from sloped surface 76.

FIG. 11 shows in isolated perspective, first and second locking parts 34 and 36 and their relative relationship when spaced apart.

It is to be understood that the included preferred embodiment is given by way of example only, and not by way of limitation to the invention, which is solely described by the claims herein. Variations obvious to one skilled in the art will be included within the invention defined by the claims.

It is to be understood that the preferred embodiment of the invention can be produced by electrical discharge machine (EDM) processes which allow accurate cutting of electrically conductive materials. One preferred material for the present preferred embodiment would be stainless steel.

What is claimed is:

1. A gripping device comprising:
   first and second elongated members each having a longitudinal axis, first and second opposite walls, and first and second opposite edges, and including a gripping end on one side of a pivot section, and a handle end on the opposite side of the pivot section;
   said first and second elongated members being pivotally and releaseably engaged at said pivot sections so that upon converging movement of the handles, the gripping ends converge to allow the gripping of an object;
   said pivot section of said first elongated member comprising a generally rectangular box aperture extending between and through the first and second walls of the first elongated member, the long axis across the box aperture extending along the longitudinal axis of the first elongated member;
   said second member being insertable through said box aperture and having a cam means integrally formed at the pivot section of the second elongated member, said cam means having front and rear bearing surfaces which form pivot surfaces of the pivot section of the second member and retain said cam in said box aperture of the pivot section of the first elongated member upon sufficient convergence of said handle ends, but which allows release of the cam from the box aperture upon sufficient separation of the handles; and
   a fulcrum means positioned outside of the pivot sections of the first and second elongated members.

2. The device of claim 1 wherein said first elongated member is angled at the location of the box aperture so that the general plane of the gripping end is offset from the general plane of the handle member of the first elongated member between their edge surfaces.

3. The device of claim 2 wherein the box, aperture is defined by front and rear walls, and opposite side walls, the front and rear walls representing the front and back of the long axis of the box aperture.

4. The device of claim 3 wherein the front and rear walls defining the box aperture include raised protrusions at their center which comprise bearing surfaces for the bearing surfaces of the cam member of the second member.

5. The device of claim 3 wherein the front and rear walls of the box aperture are in generally the planes of the gripping end and the handle end of the first member respectively.

6. The device of claim 1 wherein the cam means of the second member comprises a generally circular element with the front and rear bearing surfaces defining arcuate portions of said circle, and the other portion of the circle being truncated.

7. The device of claim 6 wherein the bearing surfaces of the second member cam means are offset from one another, said gripping end of said second member being displaced in a slightly spaced apart plane from the general plane of said handle end, with said cam member in between.

8. The device of claim 7 wherein said cam member is wider between said front and rear bearing surfaces than between the truncated sides.

9. The device of claim 1 wherein the fulcrum means comprises protrusions extend from the first interfacing walls of the handle member directly behind the pivot section, said fulcrum means serving to come into mutual abutment when said gripping ends of said first and second elongated members grip and contact an object, so that the fulcrum means experiences the major force of the converging handle members, and prevents gapping of the gripping ends.

10. The device of claim 1 wherein said handle members further comprise a rearwardmost releasable connection which retains the rearwardmost ends of the first and second elongated members when the cam means is retained within the box aperture of the pivot section and which causes the handle ends to be positioned spaced apart from one another in a normal position, which in turn biases the gripping ends to the normally open position.

11. The device of claim 10 wherein the releasable connection includes a slot in the rearward end of the second elongated member, said slot extending from the very rear end of the second member inwardly generally along its longitudinal axis; said first member having a T-shaped head on the rearward end, the downward extending leg of the T-shaped head fitting into the slot of the second elongated member.

12. The device of claim 11 wherein the rear sections of the handles of the first and second elongated members are slightly bent toward a one another.

13. The device of claim 1 further comprising a locking mechanism between the handles of the first and second elongated members, said locking member being selectively lockable upon convergence of the handles of the first and second elongated members and being releasable upon further convergence of the first and second handle members.

14. A gripping mechanism which is easily disassemblable and assemblable comprising:
   a pair of elongated members each having a longitudinal axis, each member being pivotally but releasably connected and having first and second opposite side and first and second edges;
   pivot means formed in the members for presenting pivotal retainment of the members during gripping movement of the members between a closed and a range of open positions up to a maximum open pivoted position, and allowing for separation of said members upon movement of said members past said maximum open pivoted position;
   each member including a gripping arm in front of the pivot means and a handle section behind the pivot means;
   said pivot means being comprised of a box hinge, said box hinge including a female member formed by a generally rectangular aperture in one member, said rectangular aperture having a long axis across the rectangular aperture generally aligned with the longitudinal axis of the one member and extending through and between the first and second opposite sides of the one member, said rectangular aperture being defined by front and rear walls and side walls, said front and rear walls comprising bearing surfaces;
   a male member comprising a widened portion formed integrally along the length of the other member, said widened portion having front and rear arcuate bearing surfaces which abut said bearing surfaces of the rectangular aperture when said other member is inserted through said rectangular aperture of the first member;
   said bearing surfaces serving as containing pivot surfaces when said members are pivotally moved between a closed position and a range of open positions to a maximum open pivoted position, past which said bearing surface of said male member disengages from the bearing surfaces of the female member and allow the member to be separated from the one member; and
   a fulcrum means positioned behind the pivot means for bearing pivotal forces and preventing gapping between the elongated members.

15. The gripping mechanism of claim 14 wherein the fulcrum means comprises a generally raised flat surface extending towards one another from each elongated member.

16. A selectively engageable and disengageable locking mechanism for use with instruments such as tweezers, scissors, clamping devices, and the like, which have first and second actuating handles in spaced relation to one another comprising:
   a first arm member attachable to the innerfacing surface of the first handle, said arm extending at first generally perpendicularly from said innerfacing surface and then extending generally parallel to said innerfacing surface, and having an outer end which includes a catching edge, said catching edge being generally parallel with and facing said innerfacing surface, said first arm being deflectable in direction transverse to the plane of the innerfacing surface of the first handle;
   a second arm member attachable to an innerfacing surface of the second handle, said second arm extending at first generally perpendicularly from said second arm innerfacing surface and then generally parallel to said surface in a direction opposite to that of the first arm member, said second arm having a rigidly positioned outer end which includes a sloping surface of increasing thickness from its outer edge furthest from the innerfacing surface of the second arm, its inner edge being closest to the innerfacing surface of the second arm; the inner edge of the outer end of the second arm containing a catcher edge, said catcher edge also including a small protrusion positioned so as to allow the catching edge to rest upon the catcher edge but not passed by unless additional convergence of the handles is completed;
   said first and second arms being relatively positionable on innerfacing surfaces of the first and second handles, respectively, so that upon convergence of the handles, said outer end of the first arm contacts the sloping surface of the second arm, and is deflected accordingly, until reaching the inner edge, at which point slight convergence of the
   handles will cause the catching edge of the first arm to catch and release the first and second arms and first and second handles at that converged position, still further convergence of the handles causing the first arm to return to a normal position by passing around the second arm, thereby releasing the handles to a normally opened position.

17. The device of claim 16 wherein the second arm member is both sloped and angled with respect to the first arm member so that any contact with the second arm member deflects the first arm member from its normal position, said first arm member being made of a deflectable material which then returns to its normal position after being moved out of contact with the second arm member.

* * * * *